(12) United States Patent
Drovetskaya et al.

(10) Patent No.: US 10,195,134 B2
(45) Date of Patent: *Feb. 5, 2019

(54) PERSONAL CARE COMPOSITIONS CONTAINING CATIONIC POLYMERS

(71) Applicants: DOW GLOBAL TECHNOLOGIES LLC, Midland, MI (US); UNION CARBIDE CHEMICALS & PLASTICS TECHNOLOGY LLC, Midland, MI (US)

(72) Inventors: Tatiana V. Drovetskaya, Martinsville, NJ (US); Susan L. Jordan, Collegeville, PA (US); Thomas H. Kalantar, Midland, MI (US); Mladen Ladika, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/527,062

(22) PCT Filed: Nov. 17, 2015

(86) PCT No.: PCT/US2015/061061
§ 371 (c)(1),
(2) Date: May 16, 2017

(87) PCT Pub. No.: WO2016/085707
PCT Pub. Date: Jun. 2, 2016

(65) Prior Publication Data
US 2017/0360686 A1 Dec. 21, 2017

Related U.S. Application Data

(60) Provisional application No. 62/084,143, filed on Nov. 25, 2014.

(51) Int. Cl.
*A61K 8/41* (2006.01)
*A61K 8/81* (2006.01)
(Continued)

(52) U.S. Cl.
CPC .......... *A61K 8/8158* (2013.01); *A61K 8/416* (2013.01); *A61K 8/891* (2013.01); *A61Q 5/02* (2013.01);
(Continued)

(58) Field of Classification Search
None
See application file for complete search history.

(56) References Cited

U.S. PATENT DOCUMENTS 5,338,541 A   8/1994  Matz et al.
5,609,862 A   3/1997  Chen et al.
(Continued)

FOREIGN PATENT DOCUMENTS

CA   2517317 A1   2/2006
JP   2012020968 A   2/2012
(Continued)

OTHER PUBLICATIONS

Office Action from corresponding U.S. Appl. No. 15/527,427, dated Apr. 9, 2017.

*Primary Examiner* — Aradhana Sasan
(74) *Attorney, Agent, or Firm* — Thomas S. Deibert

(57) ABSTRACT

Provided are compositions and methods that are useful for personal care compositions. The compositions comprise (a) a cationic polymer comprising polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) silicone. Also provided are methods of treating hair with such compositions.

6 Claims, 1 Drawing Sheet

(51) Int. Cl.
*A61Q 5/02* (2006.01)
*A61Q 5/12* (2006.01)
*A61K 8/891* (2006.01)
*A61Q 19/10* (2006.01)

(52) U.S. Cl.
CPC ............... *A61Q 5/12* (2013.01); *A61Q 19/10* (2013.01); *A61K 2800/5426* (2013.01); *A61K 2800/596* (2013.01)

(56) References Cited

U.S. PATENT DOCUMENTS

| | | |
|---|---|---|
| 5,637,306 A | 6/1997 | Cauwet et al. |
| 6,849,584 B2 | 2/2005 | Geary et al. |
| 7,015,279 B2 | 3/2006 | Braun et al. |
| 7,405,188 B2 | 7/2008 | Chen |
| 2003/0059382 A1 | 3/2003 | Brandt et al. |
| 2005/0100523 A1 | 5/2005 | Maubru et al. |
| 2006/0024338 A1* | 2/2006 | Hegedus ............ A61K 8/8135 424/401 |
| 2017/0354586 A1* | 12/2017 | Drovetskaya ........ A61K 8/8158 |

FOREIGN PATENT DOCUMENTS

| | | |
|---|---|---|
| WO | 200037041 A1 | 6/2000 |
| WO | 2002083085 A1 | 10/2002 |
| WO | 2004069979 A2 | 8/2004 |
| WO | 2005002532 A2 | 1/2005 |
| WO | 2006058755 A1 | 6/2006 |
| WO | 2006081496 A2 | 8/2006 |
| WO | 2007098888 A1 | 9/2007 |
| WO | 2007128639 A2 | 11/2007 |
| WO | 2009024936 A2 | 2/2009 |

* cited by examiner

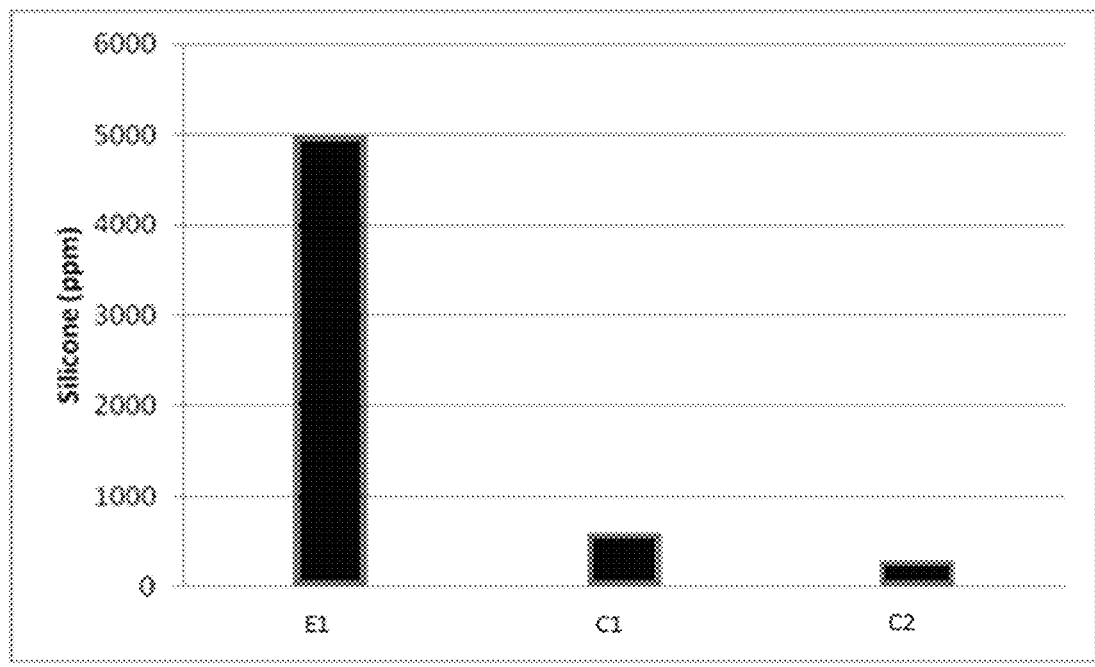

PERSONAL CARE COMPOSITIONS CONTAINING CATIONIC POLYMERS

FIELD OF THE INVENTION

This invention relates generally to cationic polymers and their use in personal care compositions. The cationic polymers contain as polymerized units cationic monomers, (meth)acrylamide monomers, and polar non-ionic derivatives of acrylic monomers.

BACKGROUND

Conditioning of hair is one of the most desired attributes in a personal care composition, particularly conditioners, shampoos, and body washes. Unless a conditioning agent is utilized, hair is often difficult to manage during and after shampooing. Similarly, there is a need for shampoos that can clean, condition, and increase hair manageability. To this end, silicones are added to shampoos.

Combinations of silicones and cationic polymers have been utilized. For example, PCT International Publication No. WO 2000/37041 discloses keratin conditioning formulations containing a water soluble, organic, ampholytic polymer and a water soluble, organic, cationic polymer. The prior art falls short, however, of delivering optimal conditioning properties while maintaining hair in a clean, non-greasy appearance after shampoo application.

Consequently, there is a continuing need to develop new cost-effective high performance conditioning agents that provide increased uniform deposition of silicones and other actives onto hair, while also providing for increased manageability.

STATEMENT OF INVENTION

One aspect of the invention provides a personal care composition comprising (a) a cationic polymer comprising polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) silicone. In certain embodiments, the personal care composition comprises the polar non-ionic derivatives of acrylic monomers in an amount of from 2 to 30 weight %. In certain embodiments, the personal care composition is a shampoo, a rinse-off conditioner, or a body wash.

In another aspect, the invention provides a method for treating hair comprising contacting hair with a personal care composition comprising (a) a cationic polymer comprising polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) silicone. In certain embodiments, the personal care composition comprises the polar non-ionic derivatives of acrylic monomers in an amount of from 2 to 30 weight %. In certain embodiments, the personal care composition is a shampoo.

BRIEF DESCRIPTION OF THE FIGURES

FIG. 1 shows the silicone deposition onto hair after washing with shampoo formulations containing inventive and comparative conditioning agents.

DETAILED DESCRIPTION

The inventors have now surprisingly found that personal care compositions containing cationic polymers containing, as polymerized units, a cationic monomer, an acrylamide monomer, and a polar non-ionic derivative of an acrylic monomer, provide increased uniform deposition of silicones and other actives onto hair, while also providing for increased manageability. Accordingly, in certain preferred embodiments the present invention provides in one aspect personal care compositions including (a) cationic polymers containing polymerized units derived from (i) 30 to 80 weight % of cationic monomers, (ii) 10 to 65 weight % of (meth)acrylamide monomers, and (iii) 0 to 30 weight % of polar non-ionic derivatives of acrylic monomers, and (b) silicone.

In the present invention, "personal care" is intended to refer to cosmetic and skin care compositions for application to the skin, including, for example, body washers and cleansers, as well as leave-on applications to the skin, such as lotions, creams, gels, gel creams, serums, toners, wipes, liquid foundations, make-ups, tinted moisturizers, oils, face/body sprays, topical medicines, and sunscreens. In the present invention, "personal care" is also intended to refer to hair care compositions including, for example, shampoos, rinse-off conditioners, leave-on conditioners, styling gels, hairsprays, mousses, pomades, hair treatment formulations, and combing creams. Preferably, the personal care compositions are cosmetically acceptable. As used herein, "cosmetically acceptable" refers to ingredients typically used in personal care compositions, and is intended to underscore that materials that are toxic when present in the amounts typically found in personal care compositions are not contemplated as part of the present invention. The personal care compositions of the invention may be manufactured by processes well known in the art, for example, by means of conventional mixing, dissolving, granulating, emulsifying, encapsulating, entrapping, or lyophilizing processes.

As used herein, the term "polymer" refers to a polymeric compound prepared by polymerizing monomers, whether of the same or a different type. The generic term "polymer" includes the terms "homopolymer," "copolymer," and "terpolymer." As used herein, the term "polymerized units derived from" refers to polymer molecules that are synthesized according to polymerization techniques wherein a product polymer contains "polymerized units derived from" the constituent monomers which are the starting materials for the polymerization reactions.

As used herein, the term "(meth)acrylate" refers to either acrylate or methacrylate, and the term "(meth)acrylic" refers to either acrylic or methacrylic.

The inventive compositions include cationic polymers that contain polymerized units derived from cationic monomers. Cationic monomers are compounds that form polymerized units in which at least one cation is covalently attached to the polymer. The anion or anions corresponding to the covalently-attached cation or cations may be in solution, in a complex with the cation, located elsewhere on the polymer, or a combination thereof. The anion corresponding to the cation of a suitable cationic monomer may be any type of anion. Some suitable anions are, for example, halides (including, for example, chloride, bromide, or iodide), hydroxide, phosphate, sulfate, hydrogen sulfate, ethyl sulfate, methyl sulfate, formate, acetate, or any mixture thereof.

In certain embodiments, the cationic monomers useful in the present invention contain a cation that is permanently in cationic form, such as, for example, a quaternary ammonium salt. Quaternary ammonium salt compounds that are suitable as cationic monomers include, for example, (meth)acrylamidealkyltrialkylammonium and [(meth)acryloyloxy]alkyltrialkylammonium quaternary compounds, and diallyldialkylammonium quaternary compounds, and mixtures thereof.

(Meth)acrylamido alkyl trialkyl ammonium and (meth) acryloyloxy alkyl trialkyl ammonium quaternary compounds have the general structure:

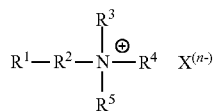

where $R^1$ is a (meth)acrylamido group, which has the general structure:

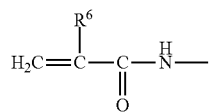

or a (meth)acryloyloxy group, which has the general structure:

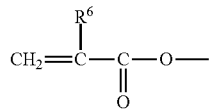

where $R^6$ is either hydrogen or a methyl group; $R^2$ is a bivalent alkyl group; each of $R^3$, $R^4$, and $R^5$ is, independently, a methyl ethyl, or butyl group; and $X^{(n-)}$ is an anion wherein n is 1, 2, or 3, for example any of the anions discussed herein above as suitable anions corresponding to cations of suitable cationic monomers. In certain embodiments, $R^6$ is hydrogen. In certain embodiments, $R^2$ is —$CH_2$—$CH_2$—$CH_2$—. Independently, in some embodiments, one, two, or all three of $R^3$, $R^4$, and $R^5$ are methyl groups. Independently, in some embodiments, $X^{(n-)}$ is a chloride ion.

Diallyldialkylammonium quaternary compounds have the general structure:

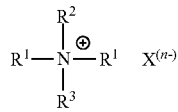

where each $R^1$ is an allyl group; each of $R^2$ and $R^3$ is, independently, an alkyl group with 1 to 3 carbon atoms; and $X^{(n-)}$ is an anion wherein n is 1, 2, or 3, for example any of the anions discussed herein above as suitable anions corresponding to cations of suitable cationic monomers. In some embodiments, each of $R^8$ and $R^9$ is a methyl group. Independently, in some embodiments, $X^{(n-)}$ is a chloride ion. In certain embodiments, the diallyldialkylammonium quaternary monomer forms a polymerized unit that is a 5-membered ring.

In certain preferred embodiments, the cationic monomer comprises at least one of diallyldimethylammonium chloride (DADMAC), [2-(acryloyloxy)ethyl]trimethylammonium chloride (AETAC), [2-(methacryloyloxy)ethyl]trimethylammonium chloride (QMA-Cl), (3-acrylamidopropyl) trimethylammonium chloride (APTAC), and (3-methacrylamidopropyl)trimethylammonium chloride (MAPTAC). In certain embodiments, the inventive cationic polymers comprise polymerized units derived from cationic monomers present in an amount of at least 30 weight %, preferably at least 35 weight %, more preferably at least 40 weight %, and even more preferably at least 45 weight %, by weight of the polymer. In certain embodiments, the inventive cationic polymers comprise the cationic monomers in an amount of no more than 80 weight %, preferably no more than 75 weight %, more preferably no more than 70 weight %, and even more preferably no more than 65 weight %, by weight of the polymer.

The inventive cationic polymers comprise polymerized units of (meth)acrylamide monomers and their derivatives. (Meth)acrylamide compounds have the general structure:

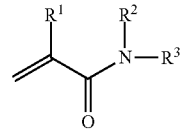

where $R^1$ is hydrogen or a methyl group; and each of $R^2$ and $R^3$ are, independently, hydrogen or a linear, branched or cyclic alkyl or aryl group having from 1 to 18 carbon atoms. In certain embodiments, the inventive cationic polymers comprise polymerized units of (meth)acrylamide monomers present in an amount of at least 10 weight %, preferably at least 15 weight %, more preferably at least 20 weight %, and even more preferably at least 25 weight %, by weight of the polymer. In certain embodiments, the inventive cationic polymers comprise the (meth)acrylamide monomers in an amount of no more than 65 weight %, preferably no more than 62.5 weight %, more preferably no more than 60 weight %, and even more preferably no more than 55 weight %, by weight of the polymer.

The inventive cationic polymers optionally comprise polymerized units of polar non-ionic derivatives of acrylic monomers. Suitable acrylic monomers include, for example, (meth)acrylic acids and their $C_1$-$C_{22}$ alkyl or hydroxyalkyl esters, including monomers of structure $H_2C$=$C(R)CO_2(CH_2CH_2O)_n(CH(R')CH_2O)_mR''$, crotonic acid, itaconic acid, fumaric acid, maleic acid, maleic anhydride, (meth) acrylamides, (meth)acrylonitrile, and alkyl or hydroxyalkyl esters of crotonic acid, itaconic acid, fumaric acid or maleic acid. In certain embodiments, the acrylic monomer comprises an aminoalkyl ester of (meth)acrylic acid, which has the general structure:

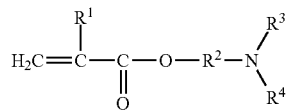

where $R^1$ is hydrogen or a methyl group; $R^2$ is a bivalent alkyl group; and each of $R^3$ and $R^4$ is, independently, a hydrogen, a methyl group, or an ethyl group. In certain embodiments, $R^1$ is a methyl group. In certain embodiments, $R^2$ is either —$CH_2$—$CH_2$— or —$CH_2$—$CH_2$—$CH_2$—. In certain embodiments, $R^3$ and $R^4$ are both methyl groups. Suitable monomers that are aminoalkyl esters of (meth) acrylic acid include, for example, 2-(dimethylamino)ethyl acrylate (DMAEA), 2-(dimethylamino)ethyl methacrylate (DMAEMA), and 3-dimethylaminopropyl acrylate (DMAPA). In certain embodiments, the inventive cationic polymers comprise polymerized units of polar non-ionic derivatives of acrylic monomers in an amount of at least 2 weight %, preferably at least 5 weight %, more preferably at least 7.5 weight %, and even more preferably at least 10 weight %, by weight of the polymer. In certain embodiments, the inventive cationic polymers comprise polymerized units of polar non-ionic derivatives of acrylic monomers in an amount of no more than 30 weight %, preferably no more than 27.5 weight %, more preferably no more than 25 weight %, and even more preferably no more than 20 weight %, by weight of the polymer.

In certain embodiments, the cationic polymer optionally further comprises polymerized units of non-polar $C_1$-$C_{22}$ alkyl (meth)acrylate monomers. Suitable non-polar monomers include, for example, methyl (meth)acrylate, butyl (meth)acrylate, 2-ethylhexyl (meth)acrylate, dodecyl (meth) acrylate, and stearyl (meth)acrylate). In certain embodiments, the inventive cationic polymers comprise polymerized units of non-polar monomers in an amount of at least 0.05 weight %, preferably at least 0.1 weight %, more preferably at least 0.5 weight %, and even more preferably at least 1.0 weight %, by weight of the polymer. In certain embodiments, the inventive cationic polymers comprise polymerized units of non-polar monomers in an amount of no more than 10 weight %, preferably no more than 8.75 weight %, more preferably no more than 7.5 weight %, and even more preferably no more than 5.0 weight %, by weight of the polymer.

Polymer molecular weights can be measured by standard methods such as, for example, size exclusion chromatography or intrinsic viscosity. In certain embodiments, the cationic polymer of the present invention has a weight average molecular weight ($M_w$) of 2,000,000 or less, preferably 1,500,000 or less, more preferably 1,250,000 or less, and even more preferably 1,000,000 or less. In certain embodiments, the cationic polymer has a $M_w$ of 50,000 or more, preferably 100,000 or more, preferably 150,000 or more, and even more preferably 250,000 or more.

The cationic polymer of the present invention may be made by any polymerization method, including, for example, solution polymerization, bulk polymerization, heterogeneous phase polymerization (including, for example, emulsion polymerization, suspension polymerization, dispersion polymerization, and inverse-emulsion polymerization), and combinations thereof. Independently, the ampholytic polymer of the present invention may be made with any type of polymerization reaction, including, for example, free radical polymerization. When solution polymerization is used, the solvent may be an aqueous solvent (i.e., the solvent is 75% or more water, by weight, based on the weight of the solvent) or an organic solvent (i.e., a solvent that is not aqueous). In certain embodiments, at least one ampholytic polymer is made by free radical solution polymerization in solution. Among such embodiments, at least one cationic polymer is made by free radical solution polymerization in an aqueous solvent.

The amount of cationic polymers in the personal care compositions of the invention may be 0.05 weight % or more, preferably 0.1 weight % or more, and more preferably 0.15 weight % or more, based on the total weight of the composition. By way of non-limiting example, the amount of cationic polymers in the personal care compositions of the invention may be 10 weight % or less, preferably 5 weight % or less, and more preferably 2.5 weight % or less, based on the total weight of the composition.

The personal care compositions of the present invention contain silicone. Suitable silicones include, for example, silicone oils (e.g., volatile or non-volatile polymethylsiloxanes (PDMS) comprising a linear or cyclic silicone chain), which are liquid or pasty at room temperature, e.g., cyclopolydimethylsiloxanes (cyclomethicones) such as cyclopentasiloxane and cyclohexadimethylsiloxane, polydimethylsiloxanes comprising alkyl, alkoxy or phenyl groups, which are pendent or at the end of a silicone chain, these groups comprising from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes 2-phenylethyltrimethyl siloxysilicates and polymethylphenylsiloxanes, fluoro oils such as partially hydrocarbon-based and/or partially silicone-based fluoro oils, preferably dimethicone, cyclopentasiloxane, cyclohexasiloxane, or a combination thereof. In certain embodiments, the silicone is a blend of dimethicone, Laureth-23, and C 12-15 Pareth-3, commercially available from Dow-Corning under the tradename DOW CORNING 2-1491 Silicone Emulsion, also described as a 60% large particle size non-ionic emulsion of a blend of ultra-high molecular weight polydimethylsiloxane gum and intermediate molecular weight polydimethylsiloxane fluid. In certain embodiments, the inventive personal care compositions include silicone in an amount of from 0.1 to 5 weight %, preferably from 0.75 to 3 weight %, and more preferably from 1 to 2 weight %, by weight of the composition.

The personal care compositions of the present invention may also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, acetone, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50% by weight of the dermatologically acceptable carrier, based on the total weight of the composition.

In certain embodiments, the personal care composition contains other optional ingredients, including, for example, other emollients (e.g., hydrocarbon oils, esters, natural oils, or fatty acids), surfactants, rheology modifiers, humectants, waxes, sensory modifiers, preservatives/antioxidants/chelating agents, reducing agents, pH adjusting agents/buffers/neutralizing agents, sunscreen actives, vitamins, proteins/amino acids, plant extracts, natural ingredients, bio-actives, fragrances/perfumes, deodorizing actives, skin exfoliating actives, topical medicament actives, infrared (IR)-absorbing materials, acne medications, foaming agents, penetrants, volatiles/propellants/solvents/carriers, liquid vehicles/solvents/carriers, salts, anti-static agents, anti-frizz agents, hair waving/straightening agents, absorbents, colorants, and hard particles. The amount of optional ingredients effective for achieving the desired property provided by such ingredients can be readily determined by one skilled in the art.

As noted above, the personal care compositions of the present invention are highly effective as conditioning agents for providing smooth hair or moisturized skin. They exhibit conditioning attributes on par with, if not better than, previously known additives for personal care applications, without the disadvantage of contributing to poor smoothness/sensory feel after deposition onto hair or skin. Accordingly, the personal care compositions of the present invention are useful for cleansing and conditioning of hair or skin. Thus, in one aspect the present invention provides that the personal care compositions may be used in a method for cleaning and conditioning hair comprising applying to the hair a shampoo composition comprising the cationic polymers described herein and silicone. In another aspect the present invention provides that the personal care compositions may be used in a method for cleaning and conditioning of skin comprising applying to the skin a composition comprising the cationic polymers described herein and silicone.

In practicing the methods of the invention, the hair care compositions are generally administered topically by applying the compositions onto the hair or skin in a conventional manner, such as by rubbing or massaging the hair or skin with the composition, and then rinsing it away with water. A person of ordinary skill in the art can readily determine the frequency with which the compositions should be applied. The frequency may depend, for example, on the amount of dirt that an individual is encountering in a given day. By way of non-limiting example, administration on a frequency of at least once per day may be desirable.

Some embodiments of the invention will now be described in detail in the following Examples.

EXAMPLES

Example 1

Preparation of Exemplary Cationic Polymer

Exemplary cationic polymers in accordance with the present invention contain the components recited in Table 1.

TABLE 1

Exemplary Cationic Polymer

| Sample | Monomer (wt %) | | |
|---|---|---|---|
| | APTAC | AAm | DMA |
| P1 (inventive) | 50.0 | 16.7 | 33.3 |

APTAC = (3-acrylamidopropyl)trimethylammonium chloride
AAm = Acrylamide
DMA = N,N-dimethylacrylamide Inventive cationic polymers were prepared in a high-throughput mode using semi-continuous parallel pressure reactor (ScPPR) manufactured by Freeslate. In the synthesis of exemplary cationic polymer P1, aqueous solutions of APTAC (0.90 g), AAm (0.30 g), and DMA (0.60 g) were used, with t-butyl hydroperoxide (t-BuOOH) and sodium formaldehyde sulfoxylate (SFS) used as an initiator in the amount of 0.15 weight % relative to the total amount of monomers. The total amount of the reaction mixture (including water) was 6.0 mL, and therefore the mixture contained 30% (wt/v) solids. The amount of residual monomers in the polymer P1 was determined by HPLC. The column Luna C18 4.6×150 mm, 3 μm, and the guard column Luna C18 3×4 mm were used. Water and acetonitrile containing 0.08% trifluoroacetic acid (TFA) were used as a mobile phase, with the following gradient: (a) Time: 0-15 min; Acetonitrile: 0-25%; (b) Time: 15-21 min; Acetonitrile: 25%; (c) Time: 21-25 min; Acetonitrile: 25-0%. A constant flow rate of 1.0 mL/min was used during the whole run. A UV detector set at 195 nm, 205 nm, or 215 nm was used. This method showed that the conversion of all three monomers was quantitative. Molecular weights of polymers were determined using gel permeation chromatography (GPC). The following parameters were used: Column: TSKgel AlphaM (7.8 mm×30 cm, 13μ); Mobile phase: 0.5M $CH_3COOH$+ 0.1M $NaNO_3$ in water; Flow Rate: 0.55 mL/min; Temperature: 25° C.; Detector: RI; Sample concentration: 1 mg/mL in mobile phase; Calibration: Poly(ethylene oxide) (PEO) standards. The $M_w$ of polymer P1 was determined to be 669,173 with a viscosity of 7,552 cps (2.0 wt % polymer solution in water).

Example 2

Preparation of Exemplary and Comparative Hair Care Compositions

Exemplary (inventive sample E1) and comparative (comparative samples C1 and C2) hair care compositions contain the components recited in Table 2.

TABLE 2

Exemplary Hair Care Compositions

| Component | INCI Name | E1 (wt %) | C1 (wt %) | C2 (wt %) |
|---|---|---|---|---|
| DI Water | DI Water | 9.03 | 13.20 | 13.20 |
| P1 (1.5%) | — | 16.67 | — | — |
| JAGUAR C-13S[1] | Cationic guar (2%)/2 hydroxy-3-(trimethylammonium)propyl ether chloride | — | 12.5 | — |
| UCARE Polymer J30M[2] | Hydroxyethyl cellulose (2%) | — | — | 12.5 |
| Standapol ES-2 (25.5%)[3] | Sodium laureth sulfate | 60.78 | 60.78 | 60.78 |
| Velvetex CDC (38.5%)[4] | Disodium cocoamphodiacetate | 6.92 | 6.92 | 6.92 |
| EGDS[5] | Ethylene glycol distearate | 2.0 | 2.0 | 2.0 |

TABLE 2-continued

Exemplary Hair Care Compositions

| Component | INCI Name | E1 (wt %) | C1 (wt %) | C2 (wt %) |
|---|---|---|---|---|
| Silicone (50% Dow Corning 1664 Emulsion)[6] | Dimethicone/Laureth-4/Laureth-23 | 2.0 | 2.0 | 2.0 |
| 10% Citric Acid | Citric acid | 2.2 | 2.2 | 2.2 |
| Glydant[7] | DMDM hydantoin | 0.4 | 0.4 | 0.4 |
| | Total | 100 | 100 | 100 |

[1]Available from Solvay
[2]Available from The Dow Chemical Company
[3]Available from BASF
[4]Available from Henkel
[5]Available from INOLEX
[6]Available from Dow Corning
[7]Available from Lonza An aqueous solution of each polymer (i.e., inventive P1, JAGUAR C-13S, and UCARE Polymer J30M) was prepared, to keep the total weight at 100 g. The polymers were hydrated for about 30 minutes at room temperature, followed by about 30 minutes at 65° C. Sodium laureth sulfate and disodium cocoamphodiacetate were added into a glass jar with a stir rod. The mixture was slowly heated to 74° C. while mixing with an overhead stirrer at approximately 500 rpm until a surfactant solution was formed. EGDS was then added while maintaining the temperature at 74° C. with stirring at approximately 500 rpm. After 15 minutes, the mixture was slowly cooled to 35° C. via a cool water bath. The Dow Corning 1664 Emulsion was slowly added to the mixture while mixing at 750 rpm; mixing was maintained for an additional 15 minutes. Each polymer (e.g., i.e., inventive P1, JAGUAR C-13S, and UCARE Polymer J30M) was then added to the polymer solution to 0.25 weight % and stirred for an additional 30 minutes. Citric acid (10 wt %) was then added to the mixture and stirred for an additional 10 minutes. Glydant and water were then added and the mixture was stirred for about 15 minutes at 500 rpm.

Example 3

Silicone Deposition Evaluation

The formulations as prepared in Examples 1 and 2 above (E1, C1, and C2) were evaluated for silicone deposition after application to hair. For each evaluation, a 5 g tress of virgin European brown hair was washed with 0.5 g of the sample formulation and rinsed at constant temperature. The hair was extracted with a 1:1 mixture of methyl butyl ketone and toluene. Atomic absorption spectroscopy was used to measure the residual silicone content of each tress and was reported as the amount of silicone (in μg)/mass of hair (in g). As shown in FIG. 1, hair tresses treated with formulations containing the inventive cationic polymers (E1) demonstrate that silicone deposition increased from 597 to 5,000 as compared with cationic guar. These results demonstrate that the inventive hair care compositions containing the inventive polymers provide superior silicone deposition performance when applied to hair.

What is claimed is:

1. A personal care composition comprising:
   (a) a cationic polymer comprising polymerized units derived from
   (i) 45 to 65 weight % of (3-acrylamidopropyl)trimethylammonium chloride (APTAC),
   (ii) 10 to 65 weight % of (meth)acrylamide monomers, and
   (iii) 2 to 30 weight % of polar non-ionic derivatives of acrylic monomers selected from the group consisting of (meth)acrylic acids and their $C_1$-$C_{22}$ alkyl or hydroxyalkyl esters, crotonic acid, itaconic acid, fumaric acid, maleic acid, maleic anhydride, (meth)acrylonitrile, and alkyl or hydroxyalkyl esters of crotonic acid, itaconic acid, fumaric acid, maleic acid, and combinations thereof; and
   (b) silicone.

2. The personal care composition of claim 1, wherein the personal care composition is a shampoo, a rinse-off conditioner, or a body wash.

3. The personal care composition of claim 1, wherein the polar non-ionic derivatives of acrylic monomers comprise at least one of 2-(dimethylamino)ethyl acrylate, 2-(dimethylamino)ethyl methacrylate, and 3-(dimethylamino)propyl acrylate.

4. The personal care composition of claim 1, wherein the cationic polymer is present in a range of from 0.05 to 10 weight %, by weight of the composition.

5. A method for treating hair comprising contacting hair with a personal care composition comprising:
   (a) a cationic polymer comprising polymerized units derived from
   (i) 45 to 65 weight % of (3-acrylamidopropyl)trimethylammonium chloride (APTAC),
   (ii) 10 to 65 weight % of (meth)acrylamide monomers, and
   (iii) 2 to 30 weight % of polar non-ionic derivatives of acrylic monomers selected from the group consisting of (meth)acrylic acids and their $C_1$-$C_{22}$ alkyl or hydroxyalkyl esters, crotonic acid, itaconic acid, fumaric acid, maleic acid, maleic anhydride, (meth)acrylonitrile, and alkyl or hydroxyalkyl esters of crotonic acid, itaconic acid, fumaric acid, maleic acid, and combinations thereof; and
   (b) silicone.

6. The method of claim 5, wherein the personal care composition is a shampoo.

* * * * *